US012773397B2

(12) United States Patent
Hasleton

(10) Patent No.: US 12,773,397 B2
(45) Date of Patent: Oct. 27, 2026

(54) TREATMENT OF SEROTONIN REUPTAKE INHIBITOR WITHDRAWAL SYNDROME

(71) Applicant: Mark Hasleton, Raanana (IL)

(72) Inventor: Mark Hasleton, Raanana (IL)

( * ) Notice: Subject to any disclaimer, the term of this patent is extended or adjusted under 35 U.S.C. 154(b) by 349 days.

(21) Appl. No.: 18/571,752

(22) PCT Filed: Jul. 6, 2022

(86) PCT No.: PCT/IB2022/056229
§ 371 (c)(1),
(2) Date: Dec. 19, 2023

(87) PCT Pub. No.: WO2023/281406
PCT Pub. Date: Jan. 12, 2023

(65) Prior Publication Data

US 2024/0277654 A1 Aug. 22, 2024

Related U.S. Application Data

(60) Provisional application No. 63/218,535, filed on Jul. 6, 2021.

(51) Int. Cl.
*A61K 31/343* (2006.01)
*A61P 39/00* (2006.01)

(52) U.S. Cl.
CPC ............ *A61K 31/343* (2013.01); *A61P 39/00* (2018.01)

(58) Field of Classification Search
CPC .................................................... A61K 31/343
See application file for complete search history.

(56) References Cited

FOREIGN PATENT DOCUMENTS

| | | | |
|---|---|---|---|
| AU | 2016228315 A1 | | 10/2016 |
| CA | 3077506 | | 4/2019 |
| WO | WO2019073388 | * | 4/2019 |

OTHER PUBLICATIONS

Keks et al., "Switching and stopping antidepressants", Australian Prescriber, vol. 39, No. 3, pp. 76-83, Jun. 1, 2016 (Jun. 1, 2016), Australian Government—Publishing Service, Canberra, AU.
Saglam et al., "Effects of escitalopram on ethanol withdrawal syndrome in rats", Progress in Neuro-Psychopharmacology & Biological Psychiatry 30 (2006) 1027-1032, Elsevier.
Foreman et al., "Antidepressant Withdrawal: A Guide for Primary Care Clinicians", The Journal for Nurse Practitioners, vol. 16, No. 3, pp. 191-194, Jan. 16, 2020 (Jan. 16, 2020), Elsevier.
Horowitz et al., "Tapering of SSRI treatment to mitigate withdrawal symptoms", The Lancet Psychiatry, published online at www.thelancet.com/psychiatry, Mar. 5, 2019, available at http://dx.doi.org/10.1016/S2215-0366(19)30032-X.
Eli Lilly & Company, highlights of prescribing information for PROZAC (fluoxetine capsules) for oral use and PROZAC (fluoxetine delayed-release capsules) for oral use, initial US approval 1987, revised Jan. 2017.
Luo et al., "National Prescription Patterns of Antidepressants in the Treatment of Adults With Major Depression in the US Between 1996 and 2015: A Population Representative Survey Based Analysis", Frontiers in Psychiatry, vol. 11 (Feb. 2020) article 35.
Warner et al., "Antidepressant Discontinuation Syndrome", American Family Physician, vol. 74, No. 3, Aug. 1, 2006, pp. 449-456, American Academy of Family Physicians.
Davies et al., "A systematic review into the incidence, severity and duration of antidepressant withdrawal effects: Are guidelines evidence-based?", Addictive Behaviors vol. 97 (2019), pp. 111-121, Elsevier.
Jha et al., "When Discontinuing SSRI Antidepressants Is a Challenge: Management Tips", Am J Psychiatry 175:12, Dec. 2018, pp. 1176-1184.
Glaxosmithkline, Highlights of FDA prescribing information for PAXIL CR (paroxetine), extended-release tablets, for oral use, Initial U.S. Approval: 1992, revised Sep. 2019.
Fava et al., "Withdrawal Symptoms after Selective Serotonin Reuptake Inhibitor Discontinuation: A Systematic Review", Psychotherapy and Psychosomatics, vol. 84 (2015), pp. 72-81, S. Karger AG.
Haddad, "Newer Antidepressants and the Discontinuation Syndrome", Journal of Clinical Psychiatry, vol. 58 (1997) supplement 7, pp. 17-22.
Ruhe et al., letter in The Lancet Psychiatry, vol. 6 (Jul. 2019) pp. 561-562, available at www.thanlancet.com/psychiatry.

* cited by examiner

*Primary Examiner* — Rei Tsang Shiao
(74) *Attorney, Agent, or Firm* — Daniel Feigelson

(57) ABSTRACT

The present invention relates to a method of treating serotonin reuptake inhibitor withdrawal syndrome comprising the administration of a therapeutically effective amount of escitalopram gentisate.

19 Claims, No Drawings

TREATMENT OF SEROTONIN REUPTAKE INHIBITOR WITHDRAWAL SYNDROME

BACKGROUND

Depression is a common illness worldwide, with more than 250 million sufferers. It affects an estimated one in fifteen adults in any given year and one in six people will experience depression at some time in their life. Especially when long-lasting and with moderate or severe intensity, depression may become a serious health condition. It can cause the affected person to suffer greatly and function poorly at work, at school and in the family. At its worst, depression can lead to suicide. Close to 800,000 people die due to suicide every year and suicide remains the second leading cause of death in 15-29 year-olds. A recent study showed an increase in the diagnosis of major depressive disorder in the US from 6% in 1996 to over 10% in 2015. The same study showed that only 70% of patients received any antidepressant therapy.

The most common treatment of depression for more than twenty years has been the oral administration of antidepressants such as serotonin reuptake inhibitors. Current estimates are that this drug class accounts for between 70 and 90% of all US antidepressant prescriptions.

Antidepressants are also among the most commonly prescribed classes of drugs in Europe and the US, with the number of prescriptions and duration of use rising year on year. Between 2000 and 2018, the UK has experienced a 170% rise in their usage with an estimation that over seven million adults in England (16% of the adult population) were being prescribed an antidepressant in 2017 and over half of these patients, had been taking the medications for longer than two years. Similar numbers can be seen in the US, where usage has risen from 8% of the population in 2002 to almost 13% (37 million adults) by 2014 with around half of these patients taking the drugs for at least five years. In both the UK and US, the average duration of antidepressant usage has also more than doubled in the ten years between 2005 and 2015.

Despite the massive increases in diagnosis of depression, the number of patients prescribed antidepressants and the duration of their usage, it is estimated that a third of patients taking the drugs for more than two years have no remaining clinical indications justifying their continued administration. The suggestion has therefore been made by both researchers and government appointed bodies, that greater consideration from prescribing physicians should be given to the possibility of discontinuing antidepressant therapy in at least part of the prescribed population.

Discontinuing oral serotonin reuptake inhibitor therapy, however, has been associated with a variety of clinical symptoms. First identified in 1997, serotonin reuptake inhibitor withdrawal syndrome comprises a wide variety of somatic and psychological symptoms including gastrointestinal complaints of nausea, vomiting and cramps, general somatic complaints of flu like symptoms and lethargy, excessive sweating or flushing, dizziness, tremors and even cognitive dysfunction such as irritability, anxiety, confusion and amnesia. The prevalence of the syndrome varies depending on the serotonin reuptake inhibitor being discontinued, but has been estimated as occurring in an average of just over half of all cases of drug discontinuance. The syndrome can also last for extended periods even after the drugs are no longer prescribed. In one study, 87% responded that the syndrome had lasted at least two months, 59% at least one year, and 16% for more than three years.

The variation in the incidence of symptoms after discontinuing a serotonin reuptake inhibitor is understood to be partly accounted for by the difference in the pharmacokinetic profiles of the individual drugs in the class. Several factors have been suggested as being relevant including a short plasma half-life and the presence of active metabolites. Despite this, even controlled release antidepressant dosage form approved product monographs warn of the possibility of developing the syndrome upon discontinuation.

Currently treatment options for serotonin reuptake inhibitor withdrawal syndrome remain limited. Re-administering the antidepressant has been shown to successfully resolve most symptoms but clearly is not a practical option for a patient looking to stop taking the medicine. Other methods include switching the patient to a different, possibly less prone, serotonin reuptake inhibitor or attempting to bridge to a non-serotonin reuptake inhibitor antidepressant before discontinuing therapy. Very often physicians will attempt to taper down the dosage of the antidepressant. Studies have shown that tapering over 14 days is not successful and the generally accepted current practise is to taper over an extended period of several months, typically four to six. Recent reports have also suggested that the tapering might need to be a hyperbolic rather than linear reduction in dose. Maintaining patient compliance for a medication they no longer wish to be taking remains a significant concern with each of these treatment approaches and managing the dose reductions when they no longer align with the available marketed doses is such a practical problem that some researchers have even suggested switching to non-regulated compounded liquid formulations.

In light of the underlying condition and the significant public health requirement to reduce the amount of unnecessary prescribing of antidepressants in the general population, there remains a need for a practical and simple solution to reduce the prevalence, duration and severity of serotonin reuptake inhibitor withdrawal syndrome.

SUMMARY OF THE INVENTION

The present invention relates to the treatment or prevention of serotonin reuptake inhibitor withdrawal syndrome comprising administering to a subject in need thereof a therapeutically effective amount of escitalopram gentisate.

DETAILED DESCRIPTION OF THE INVENTION

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

When values are expressed as approximations, by use of the antecedent "about," it will be understood that the particular value forms another embodiment. As used herein, "about X" (where X is a numerical value) preferably refers to +10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1 to 2", "1 to 2 and 4 to 5", "1 to 3 and 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded; thus, a recitation of "1 to 5" may support "1 and 3-5, but not 2", or simply "wherein 2 is not included."

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a human subject induces a desired pharmacological and/or physiologic effect by local and/or systemic action.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with respect to the particular compound, component or composition selected, the route of administration, and the ability of the components to elicit a desired result in the individual, but also with respect to factors such as the disease state or severity of the condition to be alleviated, hormone levels, age, sex, weight of the individual, metabolic rate of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide improved therapeutic response. An effective amount is also one in which any toxic or detrimental effects of the components are outweighed by the therapeutically beneficial effects.

The present invention relates to the treatment or prevention of serotonin reuptake inhibitor withdrawal syndrome comprising administering to a subject in need thereof a therapeutically effective amount of escitalopram gentisate.

As used herein, the term 'serotonin reuptake inhibitor withdrawal syndrome' refers to the set of symptoms that can occur after the discontinuation of an orally administered serotonin reuptake inhibitor that has been taken continuously for at least 1 month.

The symptoms associated with serotonin reuptake inhibitor withdrawal syndrome have been described in the published clinical literature such as Jha (2018) and Warner (2006) and can include generalized complaints, respiratory, cardiovascular, gastrointestinal, genitourinary, musculoskeletal, dermatological, neurological and psychiatric symptoms.

Generalized complaints associated with serotonin reuptake inhibitor withdrawal syndrome include chills, malaise, flu-like symptoms, fatigue, lethargy, fever, diaphoresis, blurred vision, eye movement abnormalities, sore eyes, eye twitching, tinnitus, rhinorrhea, sinus congestion, nasal congestion and increased salivation.

Respiratory symptoms complaints associated with serotonin reuptake inhibitor withdrawal syndrome include shortness of breath.

Cardiovascular symptoms complaints associated with serotonin reuptake inhibitor withdrawal syndrome include palpitations, tachycardia and elevations in systolic and diastolic blood pressure.

Gastrointestinal symptoms complaints associated with serotonin reuptake inhibitor withdrawal syndrome include nausea, vomiting, diarrhoea, abdominal pain, stomach cramps, appetite disturbances and abdominal bloating. \

Genitourinary symptoms complaints associated with serotonin reuptake inhibitor withdrawal musculoskeletal include genital hypersensitivity and premature ejaculation.

Musculoskeletal symptoms complaints associated with serotonin reuptake inhibitor withdrawal syndrome include sore muscles, myalgia, arthralgia and muscle cramps.

Dermatological symptoms complaints associated with serotonin reuptake inhibitor withdrawal syndrome include pruritus.

Neurological symptoms complaints associated with serotonin reuptake inhibitor withdrawal syndrome include disequilibrium such as vertigo, dizziness, light-headedness, gait instability, or ataxia, sensory disturbances such as unusual sensitivity to sound, electric shock-like sensations, paresthesia, numbness, tinnitus, dysgeusia or brain zaps, neuromuscular symptoms such as acute dystonia, myoclonus, tremor, shaking, Parkinsonism or akathisia and cognitive symptoms such as delirium, amnesia, memory impairments, disorientation or confusion.

Psychiatric symptoms complaints associated with serotonin reuptake inhibitor withdrawal syndrome include worsenings of mood such as dysphoria, hypomania, depression, bouts of crying, tearfulness, impulsiveness, irritability, agitation, aggression, anger attacks, mood swings, impaired concentration, muscle tension, suicidal or homicidal ideations, exacerbations of anxiety such as tension, panic or generalized anxiety, sleep disruption such as insomnia, hypersomnia, vivid dreams, nightmares or disrupted circadian rhythm and perceptual impairments such as depersonalization, derealization, hypnogogic hallucinations or unusual visual sensations such as geometric shapes and colors, auditory or visual hallucinations.

As used herein, the term 'treatment of serotonin reuptake inhibitor withdrawal syndrome' refers to the alleviation or reduction of at least one adverse or negative effect of a symptom or complaint associated with serotonin reuptake inhibitor withdrawal syndrome.

In an embodiment of the invention, the treatment of serotonin reuptake inhibitor withdrawal syndrome refers to the alleviation or reduction of at least one adverse or negative effect of any of the generalized complaints, respiratory, cardiovascular, gastrointestinal, genitourinary, musculoskeletal, dermatological, neurological or psychiatric symptoms associated with serotonin reuptake inhibitor withdrawal syndrome. In another embodiment of the invention, the treatment of serotonin reuptake inhibitor withdrawal syndrome refers to the alleviation or reduction of the majority of the adverse or negative effects of any of the generalized complaints, respiratory, cardiovascular, gastrointestinal, genitourinary, musculoskeletal, dermatological, neurological or psychiatric symptoms associated with serotonin reuptake inhibitor withdrawal syndrome. In another embodiment of the invention, the treatment of serotonin reuptake inhibitor withdrawal syndrome refers to the alleviation or reduction of all of the adverse or negative effects of any of the generalized complaints, respiratory, cardiovascular, gastrointestinal, genitourinary, musculoskeletal, dermatological, neurological or psychiatric symptoms associated with serotonin reuptake inhibitor withdrawal syndrome.

As used herein, the term 'discontinued' or 'discontinuation' refers to the abrupt cessation, or marked reduction in dose, within the preceding seven days, of an orally administered serotonin reuptake inhibitor that was taken continuously for at least 1 month.

As used herein, the term 'escitalopram gentisate' refers to the gentisic acid salt of escitalopram as described in patent application WO2019073388, the entirety of which is incorporated herein by reference.

In one embodiment of the invention, the escitalopram gentisate is crystalline. In another embodiment of the invention, the escitalopram gentisate is amorphous. In one embodiment of the invention, the escitalopram gentisate is escitalopram gentisate Form I. In another embodiment of the invention, the escitalopram gentisate is escitalopram gentisate Form II.

As used herein, the term 'prevention of serotonin reuptake inhibitor withdrawal syndrome' refers to the reduction of at least one adverse or negative effect of any of the generalized complaints, respiratory, cardiovascular, gastrointestinal, genitourinary, musculoskeletal, dermatological, neurological or psychiatric symptoms associated with serotonin reuptake inhibitor withdrawal syndrome in a subject who has discontinued their orally administered serotonin reuptake inhibitor but has yet to present with any of the complaints or symptoms associated with serotonin reuptake inhibitor withdrawal syndrome. The term applies only to the time period during which the subject is administered the escitalopram gentisate of the invention, or up to 28 days after said administration.

In one embodiment of the invention, the prevention of serotonin reuptake inhibitor withdrawal syndrome refers to the reduction of at least one adverse or negative effect of a complaint or symptom associated with serotonin reuptake inhibitor withdrawal syndrome. In another embodiment, the prevention of serotonin reuptake inhibitor withdrawal syndrome refers to the prevention of the majority of adverse or negative effects of a complaint or symptom associated with serotonin reuptake inhibitor withdrawal syndrome. In another embodiment, the prevention of serotonin reuptake inhibitor withdrawal syndrome refers to the prevention of all of the adverse or negative effects of a complaint or symptom associated with serotonin reuptake inhibitor withdrawal syndrome.

In one embodiment of the invention, the term 'orally administered serotonin reuptake inhibitors' refers to orally administered selective serotonin reuptake inhibitors (SSRIs) and selective serotonin-noradrenaline reuptake inhibitors (SNRIs). Examples of SSRIs include citalopram, escitalopram, paroxetine, sertraline, fluoxetine, fluvoxamine and their pharmaceutically acceptable salts. Examples of SNRIs include duloxetine, venlafaxine, milnacipran and their pharmaceutically acceptable salts.

In one embodiment of the invention, the subject has discontinued administration of an orally administered serotonin reuptake inhibitor prior to administration of a therapeutically effective amount of escitalopram gentisate. In a preferred embodiment, the discontinued orally administered serotonin reuptake inhibitor is selected from the group consisting of SSRIs and SNRIs. In another preferred embodiment, the discontinued orally administered serotonin reuptake inhibitor is selected from the group consisting of citalopram, escitalopram, paroxetine, sertraline, fluoxetine, fluvoxamine and their pharmaceutically acceptable salts. In another preferred embodiment, the discontinued orally administered serotonin reuptake inhibitor is selected from the group consisting of duloxetine, venlafaxine, milnacipran and their pharmaceutically acceptable salts.

In one embodiment of the invention, the subject has discontinued administration of an orally administered serotonin reuptake inhibitor that was taken continuously for at least 1 month prior to administration of a therapeutically effective amount of escitalopram gentisate. In another embodiment of the invention, the subject has discontinued administration of an orally administered serotonin reuptake inhibitor that was taken continuously for at least 6 weeks, or at least 3, 6, 12, 18, 24, 30, 36, 42, 48, 54 or 60 months prior to administration of a therapeutically effective amount of escitalopram gentisate. In a preferred embodiment of the invention, the subject has discontinued administration of an orally administered serotonin reuptake inhibitor that was taken continuously for at least 6 weeks prior to administration of a therapeutically effective amount of escitalopram gentisate. In another preferred embodiment of the invention, the subject has discontinued administration of an orally administered serotonin reuptake inhibitor that was taken continuously for at least 6 months prior to administration of a therapeutically effective amount of escitalopram gentisate. In another preferred embodiment of the invention, the subject has discontinued administration of an orally administered serotonin reuptake inhibitor that was taken continuously for at least 12 months prior to administration of a therapeutically effective amount of escitalopram gentisate. In another preferred embodiment of the invention, the subject has discontinued administration of an orally administered serotonin reuptake inhibitor that was taken continuously for at least 24 months prior to administration of a therapeutically effective amount of escitalopram gentisate.

In one embodiment of the invention, treating or preventing serotonin reuptake inhibitor withdrawal syndrome comprises administering escitalopram gentisate together with an antidepressant agent other than an SSRI or SNRI. In another embodiment of the invention, treating or preventing serotonin reuptake inhibitor withdrawal syndrome comprises administering escitalopram gentisate as the sole antidepressant agent. Examples of antidepressant agents other than SSRIs or SNRIs include tricyclic antidepressants, such as amitriptyline, imipramine and desipramine, tetracyclic antidepressants such as maprotiline, mianserin and mirtazapine, noradrenaline dopamine reuptake inhibitors such as bupropion, serotonin partial agonist-reuptake inhibitors such as vilazodone and vortioxetine, serotonin antagonists and reuptake inhibitors such as trazodone and nefazodone, NMDA receptor antagonists such as ketamine, esketamine, dextromethorphan, dextrorphan and dmethadone, noradrenaline reuptake inhibitors such as reboxetine and other agents such as pregabalin and agomelatine.

In one embodiment of the invention, the administration of escitalopram gentisate comprises the administration of a sustained release injectable pharmaceutical dosage form comprising escitalopram gentisate. In a preferred embodiment of the invention, the sustained release injectable pharmaceutical dosage form comprising escitalopram gentisate is subcutaneously administered. In another preferred embodiment of the invention, the sustained release injectable pharmaceutical dosage form comprising escitalopram gentisate is intramuscularly administered.

As used herein the term "sustained release injectable pharmaceutical dosage form" refers to an injectable dosage form that provides for the gradual release of escitalopram into the bloodstream over a period of time that is preferably at least 21 days.

The pharmaceutical dosage forms of the invention encompass dosage forms that are suitable for use with humans without undue toxic side effects. Dosage forms within the scope of the invention include the active pharmaceutical ingredient, escitalopram gentisate, and at least one pharmaceutically acceptable carrier or excipient. Examples of pharmaceutical dosage forms of the invention include, for example, microcapsules, nanocapsules, microspheres, nanospheres, microparticles, nanoparticles, polymer-drug conjugates, micelles, liposomes, hydrogels and other in-situ forming depots or implants. Said dosage forms can be formulated using biodegradable polymers or other suitable materials using methods known in the art.

Examples of biodegradable polymers useful for preparing the dosage forms of the disclosure include poly(lactide), poly(glycolide), poly(lactide-co-glycolide), poly-1-lactic acid, poly-dlactic acid, poly(glycolic acid), copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-captolactone), poly(amino acid), polyesteramide, polyanhydrides, polyphosphazines, poly(alkylene alkylate), biodegradable polyurethane, polyvinylpyrrolidone, polyalkanoic acid, polyethylene glycol, copolymer of polyethylene glycol and polyorthoester, albumin, chitosan, casein, waxes or blends or copolymers thereof.

Examples of platform technologies that are useful in preparing the sustained release pharmaceutical dosage forms of the present disclosure include those associated with Novartis (see, e.g., WO2010018159), Alkermes (see, e.g., WO200191720), Allergan (see, e.g., WO2013112434), Reckitt Benckiser (see, e.g., WO2009091737), Icon Bioscience (see, e.g., WO2013036309), Flamel Technologies (see, e.g., WO2012080986), QLT (see, e.g., WO2008153611), Rovi Pharmaceuticals (see, e.g., WO2011151356), Dong-A (see, e.g., WO2008130158), Durect (see, e.g., WO2004052336), NuPathe (see, e.g., WO2005070332), Ascendis Pharma (see, e.g., WO2011042453), Endo (see, e.g., WO2013063125), Delpor (see, e.g., WO2010105093), PolyActiva (see, e.g., WO2010040188), Flexion Therapeutics (see, e.g., WO2012019009), pSivida (see, e.g., WO2005002625), Camurus (see, e.g., WO2005117830), Bind Therapeutics (see, e.g., WO2010075072), Zogenix (see, e.g., WO2007041410), Ingell (WO2011083086), Foresee Pharmaceuticals (see, e.g., WO2008008363), Medincell (see, e.g., WO2012090070), Mapi Pharma (see, e.g., WO2011080733), DelSiTech (see, e.g., WO2008104635), OctoPlus (see, e.g., WO2005087201), Nanomi (see, e.g., WO2005115599), Peptron (see, e.g., WO2008117927), GP Pharm (see, e.g., WO2009068708), Pharmathen (see, e.g., WO2014202214), Titan Pharmaceuticals (see, e.g., WO2007139744), Tolmar (see, e.g., WO2009148580), Heron Therapeutics (see, e.g., US2014323517) and Intarcia Therapeutics (see, e.g., WO2005048952). The disclosures of each of these published international patent applications are incorporated herein by reference in their entireties. Methods for formulating an active ingredient, or a pharmaceutically acceptable salt thereof, into a dosage form of suitable for use in the instant methods are also described in, for example, Hu et al., IJPSR, 2012; vol. 3(9): 2888-2896; Hoffman, Adv. Drug. Del. Rev. 54 (2002) 3-12; AlTahami et al. Recent Patents on Drug Del. & Formulation 2007, 165-71; Pattni et al. Chem. Rev. 2015 May 26; and Wright and Burgess (ed.) Long Acting Injections and Implants (2012), the disclosures of which are incorporated herein by reference in their entireties.

In one embodiment of the invention, the administration of a sustained release injectable pharmaceutical dosage form comprising escitalopram gentisate provides for the release of therapeutically effective amounts of escitalopram into the bloodstream.

In one embodiment of the invention, therapeutically effective amounts of escitalopram in the bloodstream are provided by the administration of a single dose of escitalopram gentisate. In another embodiment of the invention, therapeutically effective amounts of escitalopram in the bloodstream are provided by the administration of multiple doses of escitalopram gentisate. In one embodiment of the invention, therapeutically effective amounts of escitalopram in the bloodstream are provided by multiple doses of escitalopram gentisate administered at least fourteen days apart from each other. In another embodiment of the invention, therapeutically effective amounts of escitalopram in the bloodstream are provided by multiple doses of escitalopram gentisate administered at least twenty-eight days apart from each other.

In one embodiment of the invention, the multiple doses of escitalopram gentisate comprise no more than five doses of escitalopram gentisate. In another embodiment of the invention, the multiple doses of escitalopram gentisate comprise no more than four doses of escitalopram gentisate. In another embodiment of the invention, the multiple doses of escitalopram gentisate comprise no more than three doses of escitalopram gentisate. In another embodiment of the invention, the multiple doses of escitalopram gentisate comprise no more than two doses of escitalopram gentisate.

As used herein, the term 'dose of escitalopram gentisate' shall refer to a single or multiple, individual, administrations of escitalopram gentisate all within a six-hour time period.

In one embodiment of the invention, the administration of escitalopram gentisate provides for therapeutically effective amounts of escitalopram in the bloodstream after the discontinuation of an orally administered serotonin reuptake inhibitor. In one embodiment of the invention, the therapeutically effective amount of escitalopram is sufficient to treat depression for a time period of at least fourteen days. In another embodiment of the invention, the therapeutically effective amount of escitalopram is sufficient to treat depression for a time period of at least twenty-eight days.

In one embodiment of the invention, blood plasma levels of escitalopram rise after administration of escitalopram gentisate to reach a maximum plasma level before gradually decreasing over time. In one embodiment of the invention, the plasma levels of escitalopram are maintained at a maximum by the administration of one or more further doses of escitalopram gentisate before gradually decreasing over time.

In one embodiment of the invention, the administration of escitalopram gentisate provides for therapeutically effective amounts of escitalopram in the bloodstream which gradually decrease over time until untraceable by standard analytical methodologies. In one embodiment of the invention, the gradual decrease of blood plasma escitalopram levels, after the administration of escitalopram gentisate, occurs for a time period of fourteen days. In another embodiment of the invention, the gradual decrease of blood plasma escitalopram levels, after the administration of escitalopram gentisate, occurs for a time period of twenty-eight days. In another embodiment of the invention, the gradual decrease of blood plasma escitalopram levels, after the administration of escitalopram gentisate, occurs for a time period of thirty-five days. In another embodiment of the invention, the gradual decrease of blood plasma escitalopram levels, after the administration of escitalopram gentisate, occurs for a time period of forty-two days. In another embodiment of the invention, the gradual decrease of blood plasma escitalopram levels, after the administration of escitalopram gentisate, occurs for a time period of forty-nine days. In another embodiment of the invention, the gradual decrease of blood plasma escitalopram levels, after the administration of escitalopram gentisate, occurs for a time period of fifty-six days. In another embodiment of the invention, the gradual decrease of blood plasma escitalopram levels, after the administration of escitalopram gentisate, occurs for a time period of sixty-three days. In another embodiment of the invention, the gradual decrease of blood plasma escitalopram levels, after the administration of escitalopram gentisate, occurs for a time period of seventy days. In another embodiment of the invention, the gradual decrease of blood plasma escitalopram levels, after the administration of escitalopram gentisate, occurs for a time period of seventy-seven days. In another embodiment of the invention, the gradual decrease of blood plasma escitalopram levels, after the administration of escitalopram gentisate, occurs for a time period of eighty-four days. In another embodiment of the invention, the gradual decrease of blood plasma escitalopram levels, after the administration of escitalopram gentisate, occurs for a time period of four months. In another embodiment of the invention, the gradual decrease of blood plasma escitalopram levels, after the administration of escitalopram gentisate, occurs for a time period of five months.

In one embodiment of the invention, the time for blood plasma levels of escitalopram to be untraceable by standard analytical methodologies is at least fourteen days, at least twenty-eight days, at least thirty-five days, at least forty-two days, at least forty-nine days, at least fifty-six days, at least sixty-three days, at least seventy days, at least seventy-seven days, at least eighty-four days, at least four months or at least five months after administration of the single or after the concluding dose of escitalopram gentisate.

In one embodiment of the invention, the doses of escitalopram gentisate are the same with each administration. In another embodiment of the invention, the doses of escitalopram gentisate are lower with each successive administration.

In one embodiment of the invention, the dose of escitalopram gentisate administered comprises no more than 600 mg escitalopram. In another embodiment of the invention, the dose of escitalopram gentisate administered comprises no more than 550 mg escitalopram. In another embodiment of the invention, the dose of escitalopram gentisate administered comprises no more than 500 mg escitalopram. In another embodiment of the invention, the dose of escitalopram gentisate administered comprises no more than 450 mg escitalopram. In another embodiment of the invention, the dose of escitalopram gentisate administered comprises no more than 400 mg escitalopram. In another embodiment of the invention, the dose of escitalopram gentisate administered comprises no more than 350 mg escitalopram. In another embodiment of the invention, the dose of escitalopram gentisate administered comprises no more than 300 mg escitalopram. In another embodiment of the invention, the dose of escitalopram gentisate administered comprises no more than 250 mg escitalopram. In another embodiment of the invention, the dose of escitalopram gentisate administered comprises no more than 200 mg escitalopram. In another embodiment of the invention, the dose of escitalopram gentisate administered comprises no more than 150 mg escitalopram. In another embodiment of the invention, the dose of escitalopram gentisate administered comprises no more than 100 mg escitalopram. In another embodiment of the invention, the dose of escitalopram gentisate administered comprises no more than 75 mg escitalopram. In another embodiment of the invention, the dose of escitalopram gentisate administered comprises no more than 50 mg escitalopram. As used herein, the term ‘mg escitalopram’ refers to the mg amount of escitalopram free base equivalent as found within a dosage form of escitalopram gentisate. For example, ‘100 mg escitalopram’ refers to 100 mg of escitalopram free base equivalent based on approximately 147.5 mg of escitalopram gentisate.

In one embodiment of the invention, the subject’s blood plasma levels of escitalopram rise to a steady state of about 20 ng/ml during the time period after the first administration of escitalopram gentisate.

As used herein, the term ‘steady state’ or ‘steady state blood plasma levels’ refers to consistent blood plasma levels over a time period of at least three days.

In one embodiment of the invention, the subject maintains steady state blood plasma levels of escitalopram of about 20 ng/ml for at least three days after administration of escitalopram gentisate. In another embodiment of the invention, the subject maintains steady state blood plasma levels of escitalopram of about 20 ng/ml for at least seven days after administration of escitalopram gentisate. In another embodiment of the invention, the subject maintains steady state blood plasma levels of escitalopram of about 20 ng/ml for at least fourteen days after administration of escitalopram gentisate. In another embodiment of the invention, the subject maintains steady state blood plasma levels of escitalopram of about 20 ng/ml for at least twenty-one days after administration of escitalopram gentisate.

In one embodiment of the invention, the subject maintains steady state blood plasma levels of escitalopram of about 20 ng/ml for at least three days after injection of escitalopram gentisate. In another embodiment of the invention, the subject maintains steady state blood plasma levels of escitalopram of about 20 ng/ml for at least seven days after injection of escitalopram gentisate. In another embodiment of the invention, the subject maintains steady state blood plasma levels of escitalopram of about 20 ng/ml for at least fourteen days after injection of escitalopram gentisate. In another embodiment of the invention, the subject maintains steady state blood plasma levels of escitalopram of about 20 ng/ml for at least twenty-one days after injection of escitalopram gentisate.

In one embodiment of the invention, the administration of escitalopram gentisate provides for a linear decrease in blood plasma levels of escitalopram over time. In another embodiment of the invention, administration of escitalopram gentisate provides for a hyperbolic decrease in blood plasma levels of escitalopram over time. In one embodiment of the invention, the administration of escitalopram gentisate provides for a linear decrease followed by a hyperbolic decrease in blood plasma levels of escitalopram over time. In one embodiment of the invention, the decrease in blood plasma levels of escitalopram over time occurs after a single dose of escitalopram gentisate. In another embodiment of the invention, the decrease in blood plasma levels of escitalopram occurs after multiple doses of escitalopram gentisate.

In one embodiment of the invention, the administration of escitalopram gentisate provides for a decrease in blood plasma levels of escitalopram over up to five months. In one embodiment of the invention, the administration of escitalopram gentisate provides for blood plasma levels of escitalopram which decrease from either a maximum plasma concentration and/or a steady state plasma concentration of about 20 ng/ml to levels untraceable by standard analytical methods after five months.

In one embodiment of the invention, one month after either maximum plasma concentration and/or a steady state plasma concentration of about 20 ng/ml, blood plasma levels of escitalopram will be approximately 16 ng/ml, after two months, approximately 12 ng/ml, after three months, approximately 8 ng/ml and after four months, approximately 4 ng/ml. In another embodiment of the invention, nineteen days after either maximum plasma concentration and/or a steady state plasma concentration of about 20 ng/ml, blood plasma levels of escitalopram will be approximately 9 ng/ml, after thirty-eight days approximately 5 ng/ml, after fifty-six days, approximately 3 ng/ml, after seventy-five days, approximately 2 ng/ml, after one hundred and thirteen days, approximately 1 ng/ml and at one hundred and thirty days, blood plasma levels of escitalopram will be less than 1 ng/ml. In another embodiment of the invention, nineteen days after either maximum plasma concentration and/or a steady state plasma concentration of about 20 ng/ml, blood plasma levels of escitalopram will be approximately 10 ng/ml, after thirty-eight days approximately 6 ng/ml, after fifty-six days, approximately 4 ng/ml, after seventy-five days, approximately 3 ng/ml, after ninety-four days, approximately 2 ng/ml, after one hundred and thirteen days, approximately 1 ng/ml and at one hundred and thirty days, blood plasma levels of escitalopram will be less than 1 ng/ml.

In one embodiment of the invention, the administration of escitalopram gentisate provides for a decrease in blood plasma levels of escitalopram over up to four months. In one embodiment of the invention, the administration of escitalopram gentisate provides for blood plasma levels of escitalopram which decrease from either a maximum plasma concentration and/or a steady state plasma concentration of about 20 ng/ml to levels untraceable by standard analytical methods after four months.

In one embodiment of the invention, one month after either maximum plasma concentration and/or a steady state plasma concentration of about 20 ng/ml, blood plasma levels of escitalopram will be approximately 15 ng/ml, after two months, approximately 10 ng/ml and after three months, approximately 5 ng/ml. In another embodiment of the invention, fifteen days after either maximum plasma concentration and/or a steady state plasma concentration of about 20 ng/ml, blood plasma levels of escitalopram will be approximately 9 ng/ml, after thirty days approximately 5 ng/ml, after forty-five days, approximately 3 ng/ml, after sixty days, approximately 2 ng/ml, after ninety days, approximately 1 ng/ml and at one hundred and five days, blood plasma levels of escitalopram will be less than 1 ng/ml. In another embodiment of the invention, fifteen days after either maximum plasma concentration and/or a steady state plasma concentration of about 20 ng/ml, blood plasma levels of escitalopram will be approximately 10 ng/ml, after thirty days approximately 6 ng/ml, after forty-five days, approximately 4 ng/ml, after sixty days, approximately 3 ng/ml, after seventy-five days, approximately 2 ng/ml, after ninety days, approximately 1 ng/ml and at one hundred and five days, blood plasma levels of escitalopram will be less than 1 ng/ml.

In one embodiment of the invention, the administration of escitalopram gentisate provides for a decrease in blood plasma levels of escitalopram over up to three months. In one embodiment of the invention, the administration of escitalopram gentisate provides for blood plasma levels of escitalopram which decrease from either a maximum plasma concentration and/or a steady state plasma concentration of about 20 ng/ml to levels untraceable by standard analytical methods after three months.

In one embodiment of the invention, one month after either maximum plasma concentration and/or a steady state plasma concentration of about 20 ng/ml, blood plasma levels of escitalopram will be approximately 13.3 ng/ml and after two months, approximately 6.7 ng/ml. In another embodiment of the invention, eleven days after either maximum plasma concentration and/or a steady state plasma concentration of about 20 ng/ml, blood plasma levels of escitalopram will be approximately 9 ng/ml, after twenty-three days approximately 5 ng/ml, after thirty-four days, approximately 3 ng/ml, after forty-five days, approximately 2 ng/ml, after sixty-eight days, approximately 1 ng/ml and at seventy-nine days, blood plasma levels of escitalopram will be less than 1 ng/ml. In another embodiment of the invention, eleven days after either maximum plasma concentration and/or a steady state plasma concentration of about 20 ng/ml, blood plasma levels of escitalopram will be approximately 10 ng/ml, after twenty-three days approximately 6 ng/ml, after thirty-four days, approximately 4 ng/ml, after forty-five days, approximately 3 ng/ml, after fifty-six days, approximately 2 ng/ml, after sixty-eight days, approximately 1 ng/ml and at seventy-nine, blood plasma levels of escitalopram will be less than 1 ng/ml.

In one embodiment of the invention, the administration of escitalopram gentisate provides for a decrease in blood plasma levels of escitalopram over up to two months. In one embodiment of the invention, the administration of escitalopram gentisate provides for blood plasma levels of escitalopram which decrease from either a maximum plasma concentration and/or a steady state plasma concentration of about 20 ng/ml to levels untraceable by standard analytical methods after two months.

In one embodiment of the invention, two weeks after either maximum plasma concentration and/or a steady state plasma concentration of about 20 ng/ml, blood plasma levels of escitalopram will be approximately 15 ng/ml, after a month, approximately 10 ng/ml and after six weeks, approximately 5 ng/ml. In another embodiment of the invention, eight days after either maximum plasma concentration and/or a steady state plasma concentration of about 20 ng/ml, blood plasma levels of escitalopram will be approximately 9 ng/ml, after fifteen days approximately 5 ng/ml, after twenty-three days, approximately 3 ng/ml, after thirty days, approximately 2 ng/ml, after forty-five days, approximately 1 ng/ml and at fifty-three days, blood plasma levels of escitalopram will be less than 1 ng/ml. In another embodiment of the invention, eight days after either maximum plasma concentration and/or a steady state plasma concentration of about 20 ng/ml, blood plasma levels of escitalopram will be approximately 10 ng/ml, after fifteen days approximately 6 ng/ml, after twenty-three days, approximately 4 ng/ml, after thirty days, approximately 3 ng/ml, after thirty-eight days, approximately 2 ng/ml, after forty-five days, approximately 1 ng/ml and at fifty three days, blood plasma levels of escitalopram will be less than 1 ng/ml.

In one embodiment of the invention, the administration of escitalopram gentisate provides for a decrease in blood plasma levels of escitalopram over up to a month. In one embodiment of the invention, the administration of escitalopram gentisate provides for blood plasma levels of escitalopram which decrease from either a maximum plasma concentration and/or a steady state plasma concentration of about 20 ng/ml to levels untraceable by standard analytical methods after a month.

In one embodiment of the invention, one week after either maximum plasma concentration and/or a steady state plasma concentration of about 20 ng/ml, blood plasma levels of escitalopram will be approximately 15 ng/ml, after two weeks, approximately 10 ng/ml and after three months, approximately 5 ng/ml. In another embodiment of the invention, four days after either maximum plasma concentration and/or a steady state plasma concentration of about 20 ng/ml, blood plasma levels of escitalopram will be approximately 9 ng/ml, after eight days approximately 5 ng/ml, after eleven days, approximately 3 ng/ml, after fifteen days, approximately 2 ng/ml, after twenty-three days, approximately 1 ng/ml and at twenty-six days, blood plasma levels of escitalopram will be less than 1 ng/ml. In another embodiment of the invention, four days after either maximum plasma concentration and/or a steady state plasma concentration of about 20 ng/ml, blood plasma levels of escitalopram will be approximately 10 ng/ml, after eight days approximately 6 ng/ml, after eleven days, approximately 4 ng/ml, after fifteen days, approximately 3 ng/ml, after nineteen days, approximately 2 ng/ml, after twenty-three days, approximately 1 ng/ml and at twenty-six days, blood plasma levels of escitalopram will be less than 1 ng/ml.

In one embodiment of the invention, the treatment of serotonin reuptake inhibitor withdrawal syndrome comprises the presentation of the subject's symptoms for less than six months after the first administration of escitalopram gentisate. In another embodiment of the invention, the treatment of serotonin reuptake inhibitor withdrawal syndrome comprises the presentation of less than 50% of the subject's symptoms for less than six months after the first administration of escitalopram gentisate. In another embodiment of the invention, the treatment of serotonin reuptake inhibitor withdrawal syndrome comprises the presentation of any of the subject's symptoms for less than six months after the first administration of escitalopram gentisate.

In one embodiment of the invention, the treatment of serotonin reuptake inhibitor withdrawal syndrome comprises the presentation of the subject's symptoms for less than five months after the first administration of escitalopram gentisate. In another embodiment of the invention, the treatment of serotonin reuptake inhibitor withdrawal syndrome comprises the presentation of less than 50% of the subject's symptoms for less than five months after the first administration of escitalopram gentisate. In another embodiment of the invention, the treatment of serotonin reuptake inhibitor withdrawal syndrome comprises the presentation of any of the subject's symptoms for less than five months after the first administration of escitalopram gentisate.

In one embodiment of the invention, the treatment of serotonin reuptake inhibitor withdrawal syndrome comprises the presentation of the subject's symptoms for less than four months after the first administration of escitalopram gentisate. In another embodiment of the invention, the treatment of serotonin reuptake inhibitor withdrawal syndrome comprises the presentation of less than 50% of the subject's symptoms for less than four months after the first administration of escitalopram gentisate. In another embodiment of the invention, the treatment of serotonin reuptake inhibitor withdrawal syndrome comprises the presentation of any of the subject's symptoms for less than four months after the first administration of escitalopram gentisate.

In one embodiment of the invention, the treatment of serotonin reuptake inhibitor withdrawal syndrome comprises the presentation of the subject's symptoms for less than three months after the first administration of escitalopram gentisate. In another embodiment of the invention, the treatment of serotonin reuptake inhibitor withdrawal syndrome comprises the presentation of less than 50% of the subject's symptoms for less than three months after the first administration of escitalopram gentisate. In another embodiment of the invention, the treatment of serotonin reuptake inhibitor withdrawal syndrome comprises the presentation of any of the subject's symptoms for less than three months after the first administration of escitalopram gentisate.

In one embodiment of the invention, the treatment of serotonin reuptake inhibitor withdrawal syndrome comprises the presentation of the subject's symptoms for less than two months after the first administration of escitalopram gentisate. In another embodiment of the invention, the treatment of serotonin reuptake inhibitor withdrawal syndrome comprises the presentation of less than 50% of the subject's symptoms for less than two months after the first administration of escitalopram gentisate. In another embodiment of the invention, the treatment of serotonin reuptake inhibitor withdrawal syndrome comprises the presentation of any of the subject's symptoms for less than two months after the first administration of escitalopram gentisate.

In one embodiment of the invention, the treatment of serotonin reuptake inhibitor withdrawal syndrome comprises the presentation of the subject's symptoms for less than a month after the first administration of escitalopram gentisate. In another embodiment of the invention, the treatment of serotonin reuptake inhibitor withdrawal syndrome comprises the presentation of less than 50% of the subject's symptoms for less than a month after the first administration of escitalopram gentisate. In another embodiment of the invention, the treatment of serotonin reuptake inhibitor withdrawal syndrome comprises the presentation of any of the subject's symptoms for less than a month after the first administration of escitalopram gentisate.

This invention will be better understood by reference to the Examples, which follow, but those skilled in the art will readily appreciate that the specific experiments detailed are only illustrative of the invention as described more fully in the claims which follow thereafter.

EXAMPLES

Example 1: Preparation of Escitalopram Base From Escitalopram Oxalate Salt

Escitalopram oxalate (40 g) and deionized water (170 ml) were introduced to a 250 ml jacketed glass reactor equipped with a mechanical stirrer, circulating oil bath and thermometer. While the mixture was stirred, 45 ml of ether was added with the jacket temperature maintained at 25° C. throughout the isolation procedure. The pH of the mixture was adjusted to 9.0-9.5 by the addition of 25% NH4OH. The stirrer was stopped to allow the settling of the mixture. Two liquid phases and solid precipitates formed. The resultant mixture was filtered and the obtained solid cake washed with 40 ml of ether. The filtrate and ether wash were then re-introduced into the reactor. Organic and aqueous phases were separated and collected into different containers. The aqueous phase was re-introduced to the reactor and extracted with 50 ml of ether. After settling, the aqueous phase was discarded. The two organic extracts were mixed in the reactor and washed twice with 25 ml of water. The organic solution was evaporated in a rotary evaporator under vacuum, with the bath temperature maintained at 70° C., until complete evaporation of solvent occurred. The resultant residue, 30.1 g of colorless clear oil (hot), was transferred to an amber glass vial.

Example 2: Preparation of Escitalopram Gentisate Form I

Two hundred (200) microliter (μl) of 100 mg/ml clear solution of escitalopram free base (as described in example 1) in methanol was added to a 4 mL vial. The methanol was evaporated by uncovering the vial. The remaining material was dried at 60° C. and dried in a vacuum for 3 to 6 h after which 500 μl of 0.125M of gentisic acid in methanol was added to the vial. Methanol was again evaporated by uncovering the vial. The material was dried at 60° C. and further dried in a vacuum for 3 to 5 h. 250 μl of isopropanol was added to the dried material in the vial. A magnetic stirrer was placed into the vial and the mixture was stirred. Whenever the stirrer was stuck by the viscous material on the bottom of the vial, the solution was sonicated or the stirrer moved with a spatula. The vial was sonicated when whitish solids were identified as stuck to the side of the vial. Stirring continued for 24 to 28 hours by which time the solution had become a thick slurry. The slurry was filtered and the obtained solid was dried at 60° C. followed by vacuum drying overnight. The sample was subject to X-ray powder diffraction (XRPD) and identified as escitalopram gentisate form I.

Example 3: Preparation of Escitalopram Gentisate Sustained Release Injectable Dosage Form A drug solution is prepared by dissolving 400 g of escitalopram gentisate in 1267 g of benzyl alcohol to form a 24 wt. % drug solution. A polymer solution is formed by dissolving 600 g of MEDISORBS 7525 DL polymer in 3000 g of ethyl acetate to form a 16.7 wt. % polymer solution. The drug solution and the polymer solution are combined to form a first, discontinuous phase. The second, continuous phase is prepared by preparing a 30l solution of 1% PVA, the PVA acting as an emulsifier. To this is added 2086 g of ethyl acetate to form a 6.5 wt. % solution of ethyl acetate.

The two phases are combined using a static mixer, such as a ½" Kenics static mixer available from Chemineer, Inc., North Andover, MA. A total flow rate of 3 l/min generally provides microparticle size distributions with a mass median diameter (MMD) in the range of about 80-90a. The ratio of continuous phase to discontinuous phase is 5:1 (v/v). The length of the static mixer can vary from about 9 inches to about 88 inches. The quench liquid is 2.5% solution of ethyl acetate and water-for-injection (WFI) at 5-10° C. The volume of the quench liquid is 0.25 l/g of batch size. The quench step is carried out for a time period greater than about 4 hours, with stirring of the microparticles in the quench tank.

After completion of the quench step, the microparticles are transferred to a collecting, dewatering, and drying device. The microparticles are rinsed using a chilled (approximately 5° C.) 17|25% ethanol solution. The microparticles are dried, and then re-slurried in a re-slurry tank using a 25% ethanol solution (extraction medium) maintained at a temperature lower than the Tg (glass transition temperature) of the microparticles. The microparticles are then transferred back to the quench tank for washing for a time period of at least 6 hours with another extraction medium (25% ethanol solution) that is maintained at a temperature higher than the Tg of the microparticles. The Tg of the microparticles is about 18° C. (about room temperature), and the temperature of the extraction medium in the quench tank is greater than about 18° C., preferably 25±1° C. The microparticles are transferred back to the collecting, de-watering, and drying device for de-watering and final drying. Drying continues for a time period greater than about 16 hours.

Example 4: Treatment and Prevention of Serotonin Reuptake Inhibitor Withdrawal Syndrome With Escitalopram Gentisate A sample population of 300 adult subjects who have been orally administered serotonin reuptake inhibitor for a continuous time period of at least one month but who have now been advised to stop therapy is identified and randomized into two groups, Group A (n=100) and Group B (n=200). All patients are screened at baseline, and subjects presenting with symptoms or signs which might be associated with serotonin reuptake inhibitor withdrawal syndrome despite being orally administered a serotonin reuptake inhibitor are excluded from the study.

At Day −1, all subjects take their final dose of an orally administered serotonin reuptake inhibitor. At Day 0, subjects in Group A are administered a sustained release injectable dosage form of escitalopram gentisate comprising 600 mg escitalopram.

All subjects are screened for symptoms or signs which might be associated with serotonin reuptake inhibitor withdrawal syndrome on Days 1, 2, 3, 4, 5, 6, 7, 14, 28, 35, 42, 49, 56, 63, 70, 77, 84, 100, 120 and 150. Subjects within Group B which present with symptoms or signs which might be associated with serotonin reuptake inhibitor withdrawal syndrome at any stage from Day 1 to Day 7 are randomized into two groups (Group B1 and Group B2) wherein Group B1 is administered a sustained release injectable dosage form of escitalopram gentisate comprising 600 mg escitalopram on the day the syndrome is identified as occurring while Group B is administered a placebo injection. Two following injections of 400 mg and 200 mg escitalopram are administered to Groups A and B1 on Days 30 and 60 respectively whilst on Days 30 and 60, Group B2 is administered a placebo injection.

The study's primary end point is a reduction in the signs and symptoms of serotonin reuptake inhibitor withdrawal syndrome in comparison to placebo when escitalopram gentisate is administered at any stage between Day 0 and Day 7 after discontinuation of an orally administered serotonin reuptake inhibitor.

Those skilled in the art will appreciate that numerous changes and modifications can be made to the preferred embodiments of the disclosure and that such changes and modifications can be made without departing from the spirit of the disclosure. It is, therefore, intended that the appended claims cover all such equivalent variations as fall within the true spirit and scope of the disclosure.

I claim:

1. A method of treating or preventing serotonin reuptake inhibitor withdrawal syndrome comprising subcutaneously or intramuscularly administering to a subject in need thereof a therapeutically effective amount of a sustained release injectable pharmaceutical dosage form comprising escitalopram gentisate.

2. The method according to claim 1, wherein prior to administering to a subject in need thereof a therapeutically effective amount of escitalopram gentisate, said subject has discontinued administration of an orally administered SSRI or SNRI.

3. The method according to claim 2, wherein the orally administered SSRI is selected from the group consisting of citalopram, escitalopram, paroxetine, sertraline, fluoxetine, fluvoxamine and their pharmaceutically acceptable salts, and the orally administered SNRI is selected from the group consisting of duloxetine, venlafaxine, milnacipran and their pharmaceutically acceptable salts.

4. The method according to claim 1, wherein prior to discontinuance, the subject has orally administered the SSRI or SNRI continuously for a time period of at least six weeks.

5. The method according to claim 4, wherein the time period is at least six months.

6. The method according to claim 1, wherein the escitalopram gentisate is the sole antidepressant agent administered to the subject.

7. The method according to claim 1, consisting of the administration of a single dose of escitalopram gentisate.

8. The method according to claim 1, comprising the administration of multiple doses of escitalopram gentisate.

9. The method according to claim 8, wherein the doses are administered at least fourteen days apart from each other.

10. The method according to claim 9, wherein the doses are administered at least twenty-eight days apart from each other.

11. The method according to claim 8, wherein the multiple administrations comprise no more than three separate administrations of escitalopram gentisate.

12. The method according to claim 8, wherein the doses of escitalopram gentisate administered are the same for each administration.

13. The method according to claim 8, wherein the doses of escitalopram gentisate administered are lowered with each administration.

14. The method according to claim 8, wherein the doses of escitalopram gentisate administered provide for a linear decrease in blood plasma levels of escitalopram over time.

15. The method according to claim 8, wherein the doses of escitalopram gentisate administered provide for a hyperbolic decrease in blood plasma levels of escitalopram over time.

16. The method according to claim 8, wherein the doses of escitalopram gentisate administered provide for a linear decrease followed by a hyperbolic decrease in blood plasma levels of escitalopram over time.

17. The method according to claim 1, wherein the subject is administered no more than 600 mg of escitalopram.

18. The method according to claim 1, wherein, following administration of the therapeutically effective amount of escitalopram gentisate, the subject maintains steady state plasma levels of escitalopram of about 20 ng/ml for at least fourteen days.

19. The method according to claim 1, wherein the treatment of serotonin reuptake inhibitor withdrawal syndrome comprises treating any of the subject's associated generalized complaints, respiratory, cardiovascular, gastrointestinal, genitourinary, musculoskeletal, dermatological, neurological or psychiatric symptoms, and the subject's symptoms present for less than six months after the first administration of escitalopram gentisate.

* * * * *